United States Patent [19]

Feinberg et al.

[11] Patent Number: 5,395,825
[45] Date of Patent: Mar. 7, 1995

[54] FERTILITY REGULATION WITH TRANSFORMING GROWTH FACTOR β

[75] Inventors: Ronald F. Feinberg, Cherry Hill, N.J.; Harvey J. Kliman, Woodbridge, Conn.

[73] Assignees: Yale University, New Haven, Conn.; Trustees of the University of Pennsylvania, Philadelphia, Pa.

[21] Appl. No.: 29,027

[22] Filed: Mar. 10, 1993

[51] Int. Cl.$^6$ .................... A61K 37/02; A61B 17/425; A61B 17/435; A61D 19/04
[52] U.S. Cl. ........................ 514/21; 514/12; 600/33; 600/34
[58] Field of Search .................... 514/12, 21; 436/510; 530/351, 852, 853, 850, 851; 600/33, 34, 35

[56] References Cited

U.S. PATENT DOCUMENTS

| | | | |
|---|---|---|---|
| 4,894,326 | 1/1990 | Matsuura et al. | 435/7 |
| 5,098,890 | 3/1992 | Gewirtz et al. | 514/44 |
| 5,104,977 | 4/1992 | Sporn | 530/399 |
| 5,158,934 | 10/1992 | Ammann et al. | 514/12 |
| 5,276,017 | 1/1994 | Feinberg et al. | 514/21 |

OTHER PUBLICATIONS

Graham et al "Mechanism of Control of Trophoblast Invasion In Situ" J. Cell Physiol. 148 228–234 1991.
Skinner et al. "Ovarian Thecal Cells Produce TGFβ Which Can Regulate Granulosa Cell Growth" Endocrinology 121(2) 786–792 1987.
Saunders et al. "Possible Roles for TGFβ1 In the Gastulating Chick Embryo" J. Cell Sci 99 617–626 1991.
Roberts et al. "TGFβ Stimulates the Expression of Fibronectin & of Both Subunits of the Human Fibronectin Receptor by Cultured Human Lung Fibroblasts" J. Biol. Chem. 263(10) 4586–4592 1988.
Rappolee et al. "Developmental Expression of PDGF, TGFα & TGFβ Genes in Preimplantation Mouse Embryos" Science 241 1823–1825 1988.
Vaughan et al., "Expression of the Genes for TGFα, EGF and the EGF Receptor During Early Pig Development", Devleopment 116: 663–669 (1992).
Rotbart, "Chapter 14: Human Enterovirus Infections: Molecular Approaches to Diagnosis and Pathogenesis", *Molecular Aspects of Picornavirus Infection and Detection* Ed. emler and Ehrenfeld 243–264 (1989).
Ekman et al., "Intracervical Instillation of PGE$_2$-Gel in Patients with Missed Abortion of Intrauterine Fetal Death," *Arch Gynecol* 233: 241–245 (1983).
Fydman et al., "Phase I Clinical Trial of Monoclonal Anti-human Chorionic Gonadotropin Antibody in Women with an Ectopic Pregnancy," *Fertil Steril* 52:734–738 (1989).
Helmer, et al., "Intraueterine Infusion of Highly Enriched Bovine Trophoblast Protein-1 Complex Exerts an Antiluteolytic Effect to Extend Corpus Luteum Lifespan in Cyclic Cattle", *J. Reprod. Fertil.* 87:89–101 (1989).
Jones, R. C. "Blastocyst Attachment in the Ovariectomized Rat Treated with an Intrauterine Injection of Luteinizing Hormone-releasing Hormone (LRH)," *Acta Endocrinol* 103: 266–268 (1983).
Kliman et al., "Purification, Characterization, and in Vitro Differentiation of Cytotrophoblasts from Human Term Placentae" *Endocrinology* 118: 1567–1582 (1986).
Stroop, et al., "Localization of Herpes Simplex Virus in the Trigeminal and Olfactory Systems During Acute and Latent Infections by in Situ Hybridization", *Lab. Invest.* 51: 27–38 (1984).

(List continued on next page.)

Primary Examiner—Jeffrey E. Russel
Assistant Examiner—Nancy J. Gromet
Attorney, Agent, or Firm—Woodcock Washburn Kurtz Mackiewicz & Norris

[57] ABSTRACT

Therapeutic and diagnostic methods of use for the growth factor transforming growth factor β, are provided by this invention. In accordance with preferred embodiments, methods of determining and improving competence of a conceptus toward uterine implantation are provided as are methods for determining female infertility in mammals.

5 Claims, No Drawings

OTHER PUBLICATIONS

Tortora, et al., "An Antisense Oligodeoxynucleotide Targeted Against the Type II$_\beta$ Regulatory Subunit mRNA of Protein Kinase Inhibits cAMP-induced Differentiation in HL-60 Leukemia Cells Without Affecting Phorbol Ester Effects", *Proc. Natl. Acad. Sci. U.S.A.* 87, 705–708 (1990).

Feinberg, et al., "Rapid Communication: Is Oncofetal Fibronectin a Trophoblast Glue for Human Inplantation?" *American J. Pathology*, 138(3): 537–543 (1991).

Graham, et al., "Localization of Transforming Growth Factor-$\beta$ at the Human Fetal-Maternal Interface: Role in Trophoblast Growth and Differentiation", *Biol. Reprod.*, 46 561–572 1992.

Hertig, A. T. and Rock, J., "A Description of 34 Human Ova Within the First 17 Days of Development", *American Journal of Anatomy*, 98, 435–493 (1956).

Skarp-Örberg et al., "Use of a Human Monoclonal Anti–Cytomegalovirus Anitbody for the Treatment of Severe Cytomegalovirus After Renal Transplantation," *Transplant Proc* 22:234 (1990).

Pengdi et al. "The Effect of Intrauterine Devices, the Stainless Steel Ring, the Copper T220, and Releasing Levonorgestrel, on the Bleeding Profile and the Morphological Structure of the Human Endometrium—A Comparative Study of Three IUDs. A Morphometric Study of 96 Cases," *Contraception* 40: 425–438 (1989).

FERTILITY REGULATION WITH TRANSFORMING GROWTH FACTOR β

BACKGROUND OF THE INVENTION

In the field of mammalian reproduction, many diagnostic procedures exist to aid the reproduction practitioner in making a diagnosis and choosing an appropriate course of action.

Currently, infertility in humans is defined as one year of unprotected coitus without conception. Approximately 10-15% of couples are affected by infertility. The risk of infertility is doubled for women between the ages of 35 to 44 as compared to women between the ages of 30 and 34. Approximately 600,000 couples sought professional help during the year 1968. However, in the early 1980's this number increased to over 2 million visits per year for infertility. Changes in fertility patterns will have a significant impact on the make-up of populations. It has been calculated that by the middle of the next century, the population in the United States will decline without immigration. Furthermore, the percent of people over the age of 65 will increase to over 23% in the next 100 years, resulting in an older and smaller work force.

In the United States, the majority of infertility can be accounted for by problems in the female. Evaluating a female for infertility can be complex. Examination of the fallopian tubes is an important early step in mammalian fertility evaluation due to the increased evidence of pelvic inflammatory disease. Currently, a hysterosalpingogram (HSG) is the procedure of choice to examine the patency of the fallopian tubes. In addition to HSG, hysteroscopy which is the direct examination of the uterus by a fiber optic device, is important to determine the presence of endometrial polyps, submucous leiomyomas, and other abnormalities within the uterus itself.

Another category of diagnostic procedures includes examination of ovarian function including ovulation and the secretion of progesterone during the luteal phase of the menstrual cycle. Ovarian function can be crudely assessed by measuring basal body temperatures during the menstrual cycle and cervical mucous testing around the time of ovulation. More accurate testing can be performed by measuring luteinizing hormone, a pituitary hormone which induces ovulation after a mid-cycle surge. Finally, serum progesterone levels can be measured to assess for normal luteal phase of the menstrual cycle.

The endometrium itself can be directly assessed by performing an endometrial biopsy three days before the suspected onset of menses. In assessing a mammalian endometrium, current gynecology and infertility physicians depend on pathologists to examine endometrial biopsies by hematoxylin and eosin staining of paraffin embedded specimens. For infertility patients, the reading of these biopsies provides information about the day of the cycle following ovulation, the adequacy of the luteal phase, and other potential data, such as infection, inflammation, or neoplasia of the endometrium. However, in most cases there is no evaluation of the functional and biochemical quality of the endometrium, and often no histologic reading to explain a patient's infertility problem.

Finally, the infertility patient can undergo endoscopic examination through an incision in the abdomen to directly visualize the external surfaces of the ovary, fallopian tubes and uterus to visualize any gross pathology which was not detected by previous examinations.

A high percentage of women who are unable to carry a pregnancy to full term undergo spontaneous abortion generally within the first six weeks. Pregnancy loss during the first six weeks has been shown to be as high as between 15 and 20%. Furthermore, the chance of a successful live birth after consecutive abortions without a live birth is only 40-50%.

In vitro fertilization (IVF) requires the removal of ova from a mammalian ovary, and exposure of these ova to sperm outside the body. Fertilization of each ovum requires that at least one living sperm penetrates the zona pellucida (outer covering) of the ovum and fuses with the pronucleus. Once this has occurred and the ova are fertilized, they can be transferred to a uterus where they can become implanted on the uterine wall. If implantation occurs, the pregnancy can proceed as if fertilization had occurred within the body. In vitro fertilization has gained widespread professional and public acceptance. However, despite the ever increasing frequency and refinement of this procedure, in vitro fertilization attempts most often do not result in pregnancy. In vitro pregnancy rates are currently only about 15 to 20 percent. For a variety of reasons, exposing the ova to sperm does not necessarily result in fertilization. Furthermore, even where the ova is fertilized, the pie;cement of the ova in a uterus usually does not result in normal implantation. The low success rate of IVF often leads to ari excessive financial and psychological burden for the infertile couple.

Other assisted reproductive technologies include two modifications of the IVF technique. The first is gamete intra-fallopian transfer (GIFT), the second is zygote intra-fallopian transfer (ZIFT). In the GIFT procedure, the retrieved oocyte and sperm are mixed together and placed back into the fallopian tube where fertilization takes place. The fertilized zygote then travels down through the fallopian tube into the endometrial cavity, where implantation may or may not take place. The ZIFT procedure allows for fertilization to take place in vitro as in standard IVF, and then the fertilized zygote is placed back in the fallopian tube where it then travels down into the uterus to implant. Finally, it is becoming realized that the hyper-stimulation protocols necessary to retrieve many oocytes from the donor woman may have deleterious effects on the endometrium itself and decrease the rates of implantation. Two basic procedures have been utilized to help overcome this problem. The first is considered non-stimulated oocyte retrieval. A single egg is retrieved, allowed to be fertilized and placed back into the fallopian tube or uterus for implantation. The other technique involves the hyper-stimulation portion of the IVF procedure to retrieve the eggs and allow for fertilization in vitro. The zygotes are then frozen to be placed back into the patient after several normal cycles, with the hope that the endometrium will be more receptive to implantation. All of these techniques attempt to maximize the quality of the eggs, zygotes produced after fertilization and the receptivity of the endometrium. Any procedure which would enhance the implantation rate above the standard 15 to 20% would have a marked positive effect on any of these technologies.

It is thus apparent that methods for improving the success rate of assisted reproductive techniques in mammals are greatly desired. Means for determining the competence of particular fertilized ova, conceptuses, toward uterine implantation is particularly desired since such means would lead to immediate improvement in the success rate of assisted reproduction. Methods for improving the competence of conceptuses toward implantation is likewise greatly desired. Additionally, methods for determining female infertility are also desired.

Contragestion, or post-coital contraception is currently practiced by two basic methods: surgical and medical. In the 1970's the "morning after pill" (diethylstilbestrol) was popular as a post-coital contraceptive method. More recently, the use of the anti-progesterone RU-486 has gained wide acceptance in Europe to terminate pregnancy soon after fertilization and implantation. During the first trimester, the most common technique to end a pregnancy is by surgical abortion. Surgical abortions generally involve cervical dilation and curettage or vacuum aspiration. Finally, after the first trimester, labor inducing medications such as oxytocin and prostaglandins can be utilized to induce premature delivery and thus the termination of pregnancy. The medical techniques described above are known to have a number of adverse reactions and potential complications. The surgical technique can lead to uterine rupture, hemorrhage, and infection.

In the United States, the commonly employed contraceptive techniques include oral steroidal contraceptives, injected or implanted steroidal contraceptives, intra-uterine devices, physical, chemical, or physico-chemical barrier techniques, withdrawal, sexual abstinence around the time of ovulation, breast feeding, and permanent sterilization. In addition to the high failure rates of some of these methods, a number of these methods have serious potential complications for the users. For example, in addition to metabolic changes induced by oral contraceptives, there is possibly an increased risk of neoplasia, nutritional disorders, cardiovascular effects, thromboembolism and even death.

Methods for effecting contraception and contragestion are greatly desired, especially methods which will exhibit low or no side effects toward the patient. Methods which will inhibit contragestion at an early stage in the chain of reproductive events are particularly desired and have long been sought by persons skilled in reproductive science.

SUMMARY OF THE INVENTION

This invention provides methods of determining competence of a conceptus toward uterine implantation comprising administering transforming growth factor $\beta$ (TGF$\beta$) to the conceptus and evaluating the level of production by the conceptus of trophoblast fibronectin. Trophoblast fibronectin production is indicative of competence. Applicants have recognized that embryo responsiveness to TGF$\beta$ is related to its overall likelihood of implantation, thus aiding in the selection of optimal embryos for implantation.

The invention also provides methods of determining female infertility in a patient suspected of infertility comprising assaying the tissue or bodily fluid of the patient for the presence of transforming growth factor $\beta$. Thus, the methods of this invention provide a tool for diagnosing mammals with infertility due to inadequate TGF$\beta$.

The invention further provides methods of increasing the success rate of assisted reproduction comprising administering transforming growth factor $\beta$ to ovum, sperm or conceptus prior to, simultaneously with, or following introduction of ovum, sperm or conceptus into the reproductive tract of a female mammal. Applicants have discovered that during normal mammalian pregnancy, trophoblast fibronectin, localized in the placental-uterine junction, is important to implantation. Thus, TGF$\beta$, which has been found to (1) concominantly stimulate the production of trophoblast fibronectin; and (2) promote adhesiveness of trophoblast to the extracellular matrix, effectively enhances the implantation of the ovum or conceptus.

The invention still further provides methods of augmenting trophoblast fibronectin synthesis in a mammal comprising administering to the mammal an effective amount of transforming growth factor $\beta$. Applicants have recognized the importance of trophoblast fibronectin in mammalian reproduction, and have discovered that augmenting the production of trophoblast fibronectin is an important method of fertility therapy. Such augmentation has been found to be effected by transforming growth factor $\beta$.

The invention also provides methods of inhibiting transforming growth factor $\beta$ synthesis in a mammal comprising administering a transforming growth factor $\beta$ inhibitor, such as antisense oligonucleotides to mRNA coding for transforming growth factor $\beta$, to the mammal. The inhibitor interferes with the production or action of the transforming growth factor $\beta$ in the mammal. Inhibiting the production or action of TGF$\beta$ by the methods of this invention provides inter alia, methods of contraception and contragestion.

The invention still further provides methods of inhibiting trophoblast fibronectin, especially tropho-uteronectin, TUN, synthesis in a mammal comprising administering a transforming growth factor $\beta$ antagonist to the mammal in an amount effective to inhibit the production or effect of the growth factor in the mammal.

The invention further provides methods of contraception and contragestion which comprise administering to a mammal a transforming growth factor $\beta$ antagonist, such as antibodies to transforming growth factor $\beta$, in an amount effective to increase the probability that conception will be prevented in said mammal. TGF$\beta$ antagonists decrease the amount of TGF$\beta$ available to stimulate, for example, TUN synthesis. This consequently renders a pregnancy unable to sustain itself and makes conception unlikely.

DETAILED DESCRIPTION OF THE INVENTION

Recently applicants have found that trophoblast fibronectins, especially tropho-uteronectin (TUN), are synthesized by trophoblasts throughout pregnancy at sites of attachment, both in vivo and in vitro. Tropho-uteronectin has been localized to the placental-uterine junction. It is believed that trophoblast fibronectins, and especially tropho-uteronectin, have a critical function in modulating trophoblast adhesion to the uterine extracellular matrix. Feinberg, et al., 1991, *American Journal of Pathology*, 38(3): 537–543. In addition, it has been established for many years that trophoblast cells of the conceptus establish contact with the uterus as a critical part of the implantation process. Hertig, A. T. and Rock, J., 1956, *American Journal of Anatomy*, 98, 435–494.

Applicants have now found that transforming growth factor $\beta$, (TGF$\beta$), stimulates the production of trophoblast fibronectin including tropho-uteronectin. Transforming growth factor $\beta$ (TGF$\beta$) as used herein is a protein released from $\alpha$-granules of platelets. TGF$\beta$ has recently been localized at the human placental-uterine interface of implantation sites surgically removed from pregnant humans. Graham, et al., 1992, Biol. Reprod., 46: 561–572. TGF$\beta$ is available commercially such as from Sigma, St. Louis, Mo., R & D Systems, Minneapolis, Minn., and Collaborative Research, New Bedford, Mass.. TGF$\beta$ refers to all of the isoforms of TGF$\beta$. Thus, TGF$\beta$1, TGF$\beta$2, TGF$\beta$3 and TGF$\beta$4 may be encompassed by some or all aspects of the present invention.

Trophoblast fibronectin includes any and all of the fibronectin proteins produced by trophoblasts. One trophoblast fibronectin, tropho-uteronectin (TUN), has been found to be particularly important to the practice of the present invention, however other trophoblast fibronectins are also believed to be important.

In accordance with the invention methods are provided for determining the competence of a conceptus toward uterine implantation comprising administering transforming growth factor $\beta$ to the conceptus and evaluating the level of production by the conceptus of trophoblast fibronectin.

By the term competence toward uterine implantation is meant characteristics important to implantation. For example, the production of fibronectin by trophoblasts is important to implantation. Thus, it is believed that the ability to elicit such response in vitro is an indication that the conceptus will effectively produce fibronectin and other factors important to development of the fetus in vivo following its introduction into the uterus.

The term "conceptus" as used herein refers to the sum of derivatives of a fertilized ovum at any stage of development from fertilization to birth, including extra-embryonic membranes, placenta, and trophoblasts, as well as the embryo or fetus. The methods of the present invention are applicable to mammals generally. For example, methods of the present invention may apply, inter alia, to bovine, equine, porcine, canine, feline and human mammals.

The level of trophoblast fibronectin produced by the conceptus can be evaluated by any method which detects the protein, but which maintains the integrity of the conceptus. Thus, evaluation may be accomplished by contacting the conceptus or the culture media surrounding the conceptus with detectably labeled antibody specific for trophoblast fibronectin. Applicants have previously demonstrated ability of cultured trophoblasts to secrete fibronectin, and more specifically TUN, into the culture media. Feinberg, et al., 1991, *American J. Pathology*, 138(3): 537–543. For example, FDC-6 is a suitable antibody which recognizes trophoblast fibronectins such as tropho-uteronectin, as disclosed in U.S. Pat. No. 4,894,326, incorporated by reference herein in its entirety. As one skilled in the art will appreciate, other antibodies which specifically recognize one or more trophoblast fibronectins may also be used.

The detectable label is conveniently selected from the group consisting of enzymes, chromophores, fluorophores, coenzymes, chemiluminescent materials, enzyme inhibitors and paramagnetic metals and radionucleotides.

An assay also expected to be suitable for use in the present invention is an in situ hybridization assay comprising the steps of contacting the conceptus with a detectably labeled oligonucleotide or cDNA probe hybridizable with mRNA coding for trophoblast fibronectin, and detecting the labeled oligonucleotide. General procedures for in situ hybridization are as described for example in Stroop, et al., 1984, *Lab. Invest.* 51:27–38 which reference is incorporated by reference herein in its entirety.

The methods of this invention may also be useful to determine female infertility in a female mammal suspected of being infertile. Accordingly, tissue or bodily fluid of a patient may be assayed for the presence of active and/or immunologic transforming growth factor $\beta$ equal to the level of a fertile control. The presence of transforming growth factor $\beta$ is indicative of fertility. The lack of transforming growth factor beta is indicative of lack of receptivity to implantation and consequently, infertility. Bodily fluids expected to be useful include, e.g., plasma, serum and cervicouterine aspirates. Examples of cell types expected to be useful in such assays include an endometrial biopsy. Generally any reproductive bodily fluid or cell type associated with implantation and the ability to stimulate synthesis of trophoblast fibronectin in a fertile control are expected to be useful. Conveniently, assays for the immunologically reactive quantity and activity of functional TGF$\beta$ are commercially available and are easily utilized by those skilled in the art.

In another aspect of this invention, methods of increasing the success rate of assisted reproduction are provided. These methods comprise administering transforming growth factor $\beta$ in vitro to a conceptus prior to introduction of said conceptus into the reproductive tract of a female mammal. Transforming growth factor $\beta$ is typically administered in doses of about 0.1 ng/ml to about 10 ng/ml. Preferably from about 0.5 ng/ml to about 5 ng/ml is administered. Still more preferably, from about 1 ng/ml to about 3 ng/ml of TGF$\beta$ is administered, the concentrations referring to the fluid in which the conceptus is suspended. In other preferred embodiments of the present invention from about 1.5 ng/ml to about 2.5 ng/ml TGF$\beta$ are administered to a conceptus. Administration can be, for example, by addition of TGF$\beta$ to the culture medium. In such case the concentrations of TGF$\beta$ refer to the final concentration in the fluid environment of the conceptus.

In another aspect of this invention, a method of augmenting trophoblast fibronectin production in a mammal is provided comprising administering to the mammal an effective amount of TGF$\beta$. Administration may be accomplished by any method known to those skilled in the art. For example, TGF$\beta$ may be administered by interuterine infusion, gels, or physiological solutions. Administration may also be accomplished systemically such as parenterally, intravenously, subcutaneously, or intradermally. For example, a "patch" which delivers TGF$\beta$ intradermally may be worn in the pubis area.

TGF$\beta$ may be administered by any one of these methods prior to the introduction of ovum, sperm, or conceptus into the reproductive tract of a female mammal, either naturally or by assisted reproductive techniques. For example, an interuterine infusion, gel or physiological solution containing TGF$\beta$ may be used to introduce TGF$\beta$ into the vagina, cervical canal, uterus, and fallopian tubes. Furthermore, in cases of assisted reproductive techniques, TGF$\beta$ may be contacted with ovum or conceptus in vitro prior to introduction into the reproductive tract.

TGF$\beta$ may also be administered simultaneously with the introduction of ovum, sperm or conceptus into the reproductive tract of a female mammal. For example, a gel may be prepared containing TGFβ in which a conceptus may be suspended during in vitro fertilization, ovum and sperm may be suspended during gamete intra-fallopian transfer or zygote may be suspending during intra-fallopian transfer. Physiological solutions containing TGFβ may also be administered contemporaneously with assisted reproductive procedures such as these.

In accordance with still other methods of the present invention, TGFβ may be administered by these methods following introduction of ovum, sperm or conceptus into the reproductive tract of a female mammal. For example, an intravenous injection of a physiological solution of TGFβ following introduction of an ovum, sperm, or conceptus into the uterus may be administered as a precautionary procedure to bolster the chances that a pregnancy will be sustained. Of course, one skilled in the art will appreciate that dosage and methods of administration will vary with the size, weight, and conditions of the patient being treated, the goal being to increase trophoblast fibronectin synthesis to levels of a normal fertile control.

In still another aspect of this invention, methods of inhibiting transforming growth factor β synthesis in a mammal are provided comprising administering a transforming growth factor β inhibitor to said mammal in an amount effective to inhibit transforming growth factor β synthesis in said mammal. For example, antisense oligonucleotides can be used to inhibit TGFβ synthesis by mammalian trophoblasts or endometrium. Recently it has been demonstrated that adding oligonucleotide antiSense DNA probes to cells causes them to specifically stop producing the corresponding protein. See, e.g., Tortora, et al. (1990), *Proc. Natl. Acad. Sci. U.S.A.* 87, 705-708. An antisense oligonucleotide can be readily made and administered in a number of ways known to those skilled in the art. See, for example, U.S. Pat. No. 5,098,890 issued Mar. 24, 1992.

Inhibition of TGFβ synthesis in a mammal has a variety of utilities. For example, a mammal determined to have a level of TGFβ equal to or in excess of a normal fertile control may be a candidate for TGFβ inhibition whereby inhibition is designed to bring levels of TGFβ within the range of a normal fertile control. TGFβ inhibition can also be employed to maintain a deficient level of TGFβ concentration as compared to a normal fertile control as a method of contraception. Additionally, TGFβ inhibition to below the level of TGFβ present in a normal fertile female can be utilized to terminate a pregnancy and thus provide a method of contragestion.

In another aspect of this invention, methods of inhibiting trophoblast fibronectin synthesis in a mammal below the level of trophoblast fibronectin found in a normal fertile female is provided comprising administering a transforming growth factor β antagonist or TGFβ receptor antagonist to said mammal in an amount effective to inhibit trophoblast fibronectin synthesis in said mammal. For example, antibodies against TGFβ or TGFβ receptors may be administered to said mammal. Such antibodies can be prepared by standard methods known to those skilled in the art. Alternatively, such antibodies are available commercially such as from R & D Systems, Minneapolis, Minn., and may be administered by well known methods.

Immunologic interruption of pregnancy can be achieved. For example, it has been shown that when 5 and 25 mg of purified anti-hCG was injected into three patients with ectopic pregnancies, one of the patients completely resolved her tubal pregnancy, while the two others had markedly decreased levels of progesterone and estrogen, suggesting a marked decrease in viability of the pregnancy. Frydman et al, "Phase I clinical trial of monoclonal anti-human chorionic gonadotropin antibody in women with an ectopic pregnancy," *Fertil Steril* 52:734-8 (1989). These authors used mouse monoclonal antibodies. In a more recent article using human monoclonal antibodies, it was shown that humanized antibodies could be utilized in the treatment of CMV after renal transplantation. Skarp et al., "Use of a human monoclonal anti-cytomegalovirus antibody for the treatment of severe cytomegalovirus after renal transplantation," *Transplant Proc* 22:234 (1990).

In addition to being given systemically, these particular monoclonal antibodies can also be applied directly within the intrauterine cavity and possibly within the fallopian tube as described above.

Administration of TGFβ and inhibitors and antagonists thereof can be accomplished as described above, for example, parenterally, by intravenous injection, by interuterine infusions, gels, or sponges or in other ways apparent to persons of skill in the art. Literature is known describing use of these methods for treatment of a variety of conditions. It has been shown that the endocrine function of an ovary can be markedly changed by an intrauterine infusion. Helmer, et al., 1989, *J. Reprod. Fertil.*, 87:89-101. It has been shown that rat uteri which received an intrauterine injection of luteinizing releasing hormone had a significantly increased rate of implantation compared to uteri which had no injection. Jones, R. C. "Blastocyst attachment in the ovariectomized rat treated with an intrauterine injection of luteinizing hormone-releasing hormone (LRH)," *Acta Endocrinol* (Copenh) 103:266-8 (1983). In addition to the use of solutions, the use of gels which are instilled intracervically to facilitate labor and delivery is known. See e.g., Ekman et al., "Intracervical instillation of PGE2-gel in patients with missed abortion or intrauterine fetal death," *Arch Gynecol* 233:241-5 (1983). Additionally, an intrauterine vehicle either similar to those currently existing on the market or modified to facilitate slower release of a pharmacologic agent which might either enhance or decrease the synthesis of TGFβ or TUN can be utilized. An example of such a slow release intrauterine vehicle can be found in et al. "The effect of intrauterine devices, the stainless steel ring, the copper T220, and releasing levonorgestrel, on the bleeding profile and the morphological structure of the human endometrium—a comparative study of three IUDs. A morphometric study of 96 cases," *Contraception* 40:425-38 (1989).

Kits for determining fibronectin production are also provided in accordance with the present invention comprising transforming growth factor β in a physiologically acceptable solution and an assay for trophoblast fibronectin. Conventional kit components such as buffering agents, antibacterial agents, stabilizing agents and excipient are also encompassed in kits of the present invention. Such components are well known in the art and are discussed, for example, in *The United States Pharmacopeia—The National Formulary*, 22nd Revision, Jan. 1, 1990, Mack Publishing Company, Easton, Pa., *Remington's Pharmaceutical Sciences*, Gennaro, A. R., ed., Mack Publishing Company, Easton, Pa. (1985), the disclosures of each of which are hereby incorporated herein by reference in their entirety.

The following examples are merely illustrative of the present invention and should not be considered as limiting the scope of the invention in any way. These examples and equivalents thereof will become more apparent to those versed in the art in light of the present disclosure, and the accompanying claims.

EXAMPLE 1

Cell Culture

Cytotrophoblasts were prepared from a normal term placenta by the method of Kliman et al., 1986, *Endocrinology*, 118: 1567–1582. Isolated trophoblasts were counted as described in Kliman, supra. Prior to cell plating, trophoblasts were suspended in Dulbecco's minimal essential media (DMEM) with added glutamine and gentamicin, with or without serum. The concentration of this cell suspension prior to plating was $2 \times 10^6$/ml.

EXAMPLE 2

Identification of a Platelet Derived TUN Stimulating Factor in Serum

On glass or plastic substrates, trophoblast cell cultures were prepared as described in Example 1. The production of TUN by trophoblasts in serum-containing medium was observed by culturing trophoblasts in different concentrations of serum. The production of TUN was determined to be dose-dependent, with concentrations of detectable TUN in the media increasing stepwise from 1 to 20 µg/ml as the amount of serum in the media was increased stepwise from 1 to 10%. One percent to 10% serum-containing media produced cells which appeared morphologically identical, with good evidence of spreading and formation of aggregates and syncytia. No TUN production was observed when trophoblasts are cultured in serum-free media and in the absense of TGFβ.

The use of a cord serum sample from a baby with severe alloimmune thrombocytopenia (severe lack of platelets) resulted in very little TUN stimulation, suggesting that a critical TUN stimulating factor is platelet derived.

To verify that TUN stimulating factor was in fact derived from platelets, blood was drawn from a healthy donor, and separated into two centrifuge tubes with anti-coagulant added. One tube was spun at high speed (2000 rpm×10 min). The other tube was spun at low speed (500 rpm×10 min). The high speed tube had no platelets in the supernatant and the low speed tube had virtually all platelets remaining in the supernatant. Both plasmas were induced to clot and the resultant serum were labeled as platelet rich (low speed spin) and platelet poor (high speed spin). Only the platelet rich serum induced trophoblasts to make increasing amounts of TUN.

EXAMPLE 3

Stimulation of TUN by Addition of TGFβ

Trophoblasts prepared as described in Example 1 were cultured in 2% platelet poor serum or in serum derived from the alloimmune thrombocytopenic neonate in the presence of exogenously added TGFβ1. 50 and 200 pM TGFβ elicited a response of 3 to 4 fold induction of TUN after 48 hours, with levels of TUN in the media increasing from approximately 1 µg/ml to 4 µg/ml.

EXAMPLE 4

TGFβ Antagonist Inhibits Production of TUN

Platelet-rich serum was preincubated separately for 6 hours with two different commercially available TGFβ neutralizing antibodies (R & D Systems, Minneapolis, Minn.) at concentrations of 50 to 100 µg/ml. Trophoblasts prepared as described in Example 1 using serum preincubated with the TGFβ neutralizing antibodies exhibited undetectable levels of TUN synthesis by Western immunoblots. (Addition of 1 ng/ml platelet-derived growth factor to trophoblast cultures for 48 hours either alone or in combination with 1 ng/ml TGFβ, had no additive effect on TUN production). This finding further confirms that TGFβ has a significant role in the stimulation of TUN.

EXAMPLE 5

Preparation of Plates

Six-well plastic dishes were precoated with a solution of plasma fibronectin (Boehringer) prepared at a concentration of 10 µg/ml in phosphate buffered saline. One ml of this solution was applied to each six well dish. The plates were incubated at room temperature for 8 to 10 hours.

EXAMPLE 6

Effect of added TGFβ on trophoblast attachment

The effect of TGFβ on trophoblast attachment to plasma fibronectin surfaces was examined. One ml of cell suspension in serum-free media prepared as described in Example 1 was added to each dish of a six well dish prepared as described in Example 5. Following plating of the cells, a stock solution (1 ng/µl) of transforming growth factor β (R & D Systems, Minneapolis, Minn.) was added to the cell culture giving a final concentration of 1 ng/ml in the trophoblast cultures which received TGFβ.

Cells were cultured for 48 hours. Thereafter medium was removed, the cultures were washed gently with PBS and fixed with 10% neutral buffered formalin for 10 minutes. Detailed examination of the cells by light microscopy revealed a clear quantitative difference between cells treated with TGFβ and those not treated with TGFβ. In the absence of pre-coated plasma fibronectin, about 97% of the cells were round. With added plasma fibronectin, coated at 10 µg/ml, about 70% of the cells were round, the remainder divided between intermediate and flat. With the addition of 1 ng/ml of acid activated TGFβ, less than 25% of the cells were round, almost 40% were intermediate, and about 35% of the cells were flat. These results suggest that the combination of both pre-coated plasma fibronectin, and added TGFβ, which stimulates trophoblast secretion of TUN, are capable of enhancing trophoblast attachment to culture surfaces under serum free conditions.

Further, the pre-coated fibronectin was found to be easily degraded by the trophoblasts, releasing into the media several proteolytic fragments. Conversely, pre-coated amniotic fluid and trophoblast fibronectin were very resistant to digestion by trophoblasts and scant levels of proteolytic fragments were found. This may explain how trophoblasts can simultaneously invade and digest the maternal uterine extracellular matrix, yet synthesize and deposit new TUN-containing, protease resistant extracellular matrix components during implantation.

What is claimed is:

1. A method of increasing the success rate of assisted implantation comprising administering transforming growth factor $\beta$ to an ovum or conceptus prior to introduction of said ovum or conceptus into the reproductive tract of a female mammal.

2. The method of claim 1 wherein from about 0.1 ng/ml to about 10 ng/ml transforming growth factor $\beta$ is administered to a conceptus.

3. A method of increasing the success rate of assisted implantation comprising administering transforming growth factor $\beta$ to the reproductive tract of a female mammal prior to introduction of ovum, sperm or conceptus into the reproductive tract of a female mammal.

4. A method of increasing the success rate of assisted implantation comprising administering transforming growth factor $\beta$ simultaneously with introduction of ovum, sperm or conceptus into the reproductive tract of a female mammal.

5. A method of increasing the success rate of assisted implantation comprising administering transforming growth factor $\beta$ following introduction of ovum, sperm or conceptus into the reproductive tract of a female mammal.

* * * * *

UNITED STATES PATENT AND TRADEMARK OFFICE
CERTIFICATE OF CORRECTION

PATENT NO. : 5,395,825
DATED      : March 7, 1995
INVENTOR(S): Feinberg et al.

It is certified that error appears in the above-identified patent and that said Letters Patent is hereby corrected as shown below:

Column 2, line 28, delete "pie;cement" and insert therefor --placement--;
Column 2, line 30, delete "ari" and insert therefor --an--;
Column 4, line 60, delete "38(3):" and insert therefor --138(3):--;
Column 8, line 49, before the words "et al." insert the word --Zhu--.

Signed and Sealed this

Third Day of October, 1995

BRUCE LEHMAN

*Attest:*

*Attesting Officer*        *Commissioner of Patents and Trademarks*